US00PP34644P2

(12) United States Plant Patent
Geerlings

(10) Patent No.: US PP34,644 P2
(45) Date of Patent: Oct. 11, 2022

(54) ***ALSTROEMERIA* PLANT NAMED 'ZAPRICLARE'**

(50) Latin Name: *Alstroemeria hybrida*
Varietal Denomination: Zapriclare

(71) Applicant: Dave Nicolaas Gerardus Geerlings, Sassenheim (NL)

(72) Inventor: Dave Nicolaas Gerardus Geerlings, Sassenheim (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 17/694,473

(22) Filed: Mar. 14, 2022

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Alstroemeria* plant named 'Zapriclare', characterized by its compact, upright to outwardly spreading and uniformly mounded plant habit; vigorous growth habit; variegated green-colored leaves with light yellow green-colored margins; numerous white-colored flowers; and excellent container and garden performance.

2 Drawing Sheets

Figure 1:
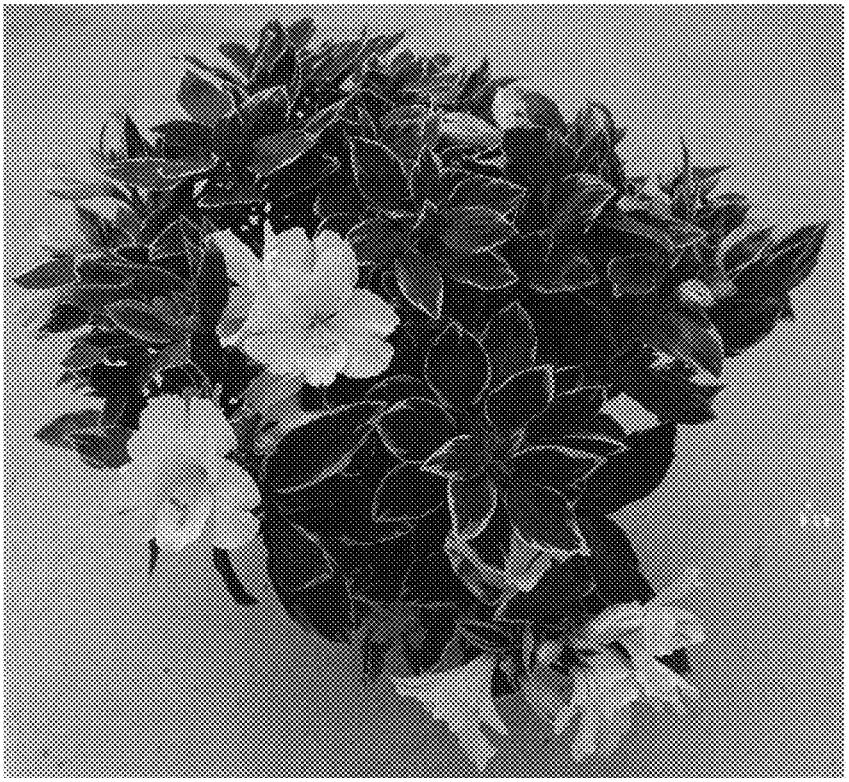

Botanical designation: *Alstroemeria hybrida.*
Cultivar denomination: 'ZAPRICLARE'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Alstroemeria* plant, botanically known as *Alstroemeria hybrida*, commercially used as a potted and garden-type *Alstroemeria*, and hereinafter referred to by the name 'Zapriclare'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant is a naturally-occurring whole plant mutation of *Alstroemeria hybrida* 'Zapriclair', disclosed in U.S. Plant Pat. No. 25,588. The new *Alstroemeria* plant was discovered and selected by the Inventor as a single flowering plant from within a population of plants of 'Zapriclair' in a controlled greenhouse environment in Rijsenhout, The Netherlands in May, 2018.

Asexual reproduction of the new *Alstroemeria* plant by rhizome divisions in a controlled greenhouse environment in Rijsenhout, The Netherlands since September, 2018 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Zapriclare'. These characteristics in combination distinguish 'Zapriclare' as a new and distinct *Alstroemeria* plant:

1. Compact, upright to outwardly spreading and uniformly mounded plant habit.
2. Vigorous growth habit.
3. Variegated green-colored leaves with light yellow green-colored margins.
4. Numerous white-colored flowers.
5. Excellent container and garden performance.

Plants of the new *Alstroemeria* can be compared to plants of the mutation parent, 'Zapriclair'. Plants of the new *Alstroemeria* differ from plants of 'Zapriclair' primarily in leaf color as plants of the new *Alstroemeria* have variegated leaves whereas plants of 'Zapriclair' have solid green-colored leaves.

Plants of the new *Alstroemeria* can be compared to plants of the variegated *Alstroemeria hybrida* 'Zaprifabi', disclosed in U.S. Plant Pat. No. 17,991. In side-by-side comparisons, plants of the new *Alstroemeria* differ primarily from plants of 'Zaprifabi' in flower color as plants of the new *Alstroemeria* have white-colored flowers whereas plants of 'Zaprifabi' have pale yellow-colored flowers. In addition, flowers of plants of the new *Alstroemeria* have fewer stripes than flowers of plants of 'Zaprifabi'.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant. %p The photograph on the first sheet (FIG. 1) is a side perspective view of a typical flowering plant of 'Zapriclare' grown in a container.

Figure 2:
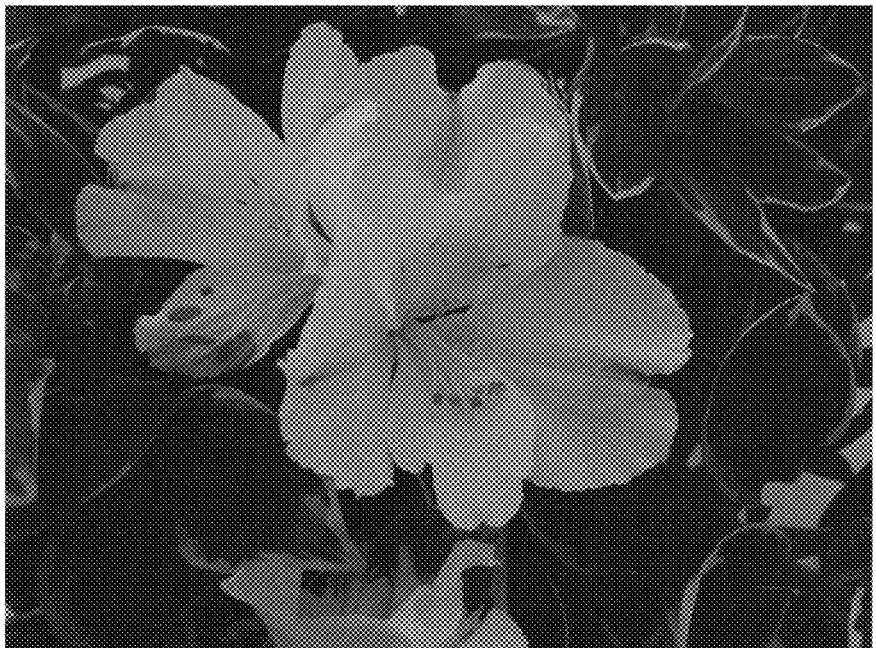

The photograph on the second sheet (FIG. 2) is a close-up view of typical leaves and flowers of 'Zapriclare'.

DETAILED BOTANICAL DESCRIPTION

The aforementioned photographs and following observations and measurements describe plants of the new *Alstroemeria* grown during the spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Zapriclare'.

Parentage: Naturally-occurring whole plant mutation of *Alstroemeria hybrida* 'Zapriclair', disclosed in U.S. Plant Pat. No. 25,588.

Propagation:

*Type*.—In vitro rhizogenesis.

*Time to produce a rooted young plant, summer*.—About 40 days at temperatures of 16° C. to 25° C.

*Time to produce a rooted young plant, winter*.—About 60 days at temperatures of 16° C. to 20° C.

*Root description*.—Fibrous, fleshy, thick; color, close to 155D.

*Rooting habit*.—Freely branching; medium density.

*Rhizomes*.—Shape: Elongate; rounded. Length: About 10 cm to 30 cm. Diameter: About 3 mm to 10 mm. Texture and luster: Smooth; matte. Color: Close to 155D.

Plant description:

*Plant and growth habit*.—Compact, upright, somewhat outwardly spreading and uniformly mounding plant habit; freely branching habit, dense and bushy appearance; vigorous growth habit and rapid growth rate.

*Plant height, soil level to top of foliar plane*.—About 23 cm.

*Plant height, soil level to top of floral plane*.—About 25 cm.

*Plant diameter* (*spread*).—About 45 cm to 50 cm.

Lateral branch description:

*Length*.—About 20 cm to 22 cm.

*Diameter*.—About 3 mm.

*Internode length*.—About 1.5 cm to 2.5 cm.

*Strength*.—Moderately strong.

*Aspect*.—About 30° to 45° from vertical.

*Texture and luster*.—Smooth, glabrous; semi-glossy.

*Color, developing and developed*.—Close to 138C.

Leaf description:

*Appearance*.—Alternate, simple.

*Length*.—About 7 cm to 9 cm.

*Width*.—About 2.5 cm to 3.5 cm.

*Shape*.—Lanceolate.

*Apex*.—Acute.

*Base*.—Attenuate.

*Margin*.—Entire.

*Texture and luster, upper and lower surfaces*.—Smooth, glabrous; semi-glossy.

*Venation pattern*.—Parallel.

*Color*.—Developing leaves, upper surface: Close to 146C and towards the margins, close to 150C. Developing leaves, lower surface: Close to 144A and towards the margins, close to 150C. Fully expanded leaves, upper surface: Close to 144A and towards the margins, close to 150C; venation, close to 141D. Fully expanded leaves, lower surface: Close to 143C and towards the margins, close to 149D; venation, close to 137D.

*Petioles*.—Length: About 2 cm to 2.5 cm. Diameter: About 4 mm to 5 mm. Strength: Moderately strong. Texture and luster, upper and lower surfaces: Smooth, glabrous; semi-glossy. Color, upper surface: Close to 138B. Color, lower surface: Close to 139C.

Flower description:

*Flower type and habit*.—Single cup-shaped flowers arranged in compound umbels; flowers face upright to outwardly; perianth segments separate; freely flowering habit with five to seven flowers per inflorescence and about 40 to 45 flowers developing per plant during the flowering season.

*Natural flowering season*.—Flowering continuous during the spring and summer in The Netherlands; early flowering habit, plants begin flowering about 70 to 80 days after planting.

*Fragrance*.—None detected.

*Flower longevity on the plant*.—About 1.5 weeks; flowers not persistent.

*Flower buds*.—Length: About 4.3 cm to 4.5 cm. Diameter: About 2 cm to 2.5 cm. Shape: Roughly ovoid. Texture and luster: Smooth, glabrous; semi-glossy. Color: Close to 143D.

*Umbel height*.—About 10 cm to 12 cm.

*Umbel diameter*.—About 14 cm to 15 cm.

*Flower diameter*.—About 7.5 cm to 8 cm.

*Flower depth*.—About 6.5 cm.

*Perianth*.—Arrangement: Six arranged in two whorls, each whorl with two lateral and one median segments. Inner perianth, lateral segments: Length: About 5.5 cm. Width: About 2.5 cm. Shape: Oblanceolate. Apex: Wishbone-shaped and caudate. Base: Attenuate. Margin: Shallowly serrated; slightly undulate. Texture and luster, upper and lower surfaces: Smooth, glabrous; matte. Color, when opening, upper and lower surfaces: Close to 155C. Color, fully opened, upper surface: Close to NN155B to NN155C; at the apex, close to 146C; towards the base, close to 8D; stripes, close to 185B; venation, close to 148D; color does not change with subsequent development. Color, fully opened, lower surface: Close to NN155C to NN155D; towards the base, close to 11D; color does not change with subsequent development. Inner perianth, median segment: Length: About 5 cm. Width: About 2.5 cm. Shape: Oblanceolate. Apex: Wishbone-shaped and caudate. Base: Attenuate. Margin: Shallowly serrated; slightly undulate. Texture and luster, upper and lower surfaces: Smooth, glabrous; matte. Color, when opening, upper and lower surfaces: Close to 155A. Color, fully opened, upper surface: Close to NN155A; at the apex, close to 146C; venation, close to 148D; color does not change with subsequent development. Color, fully opened, lower surface: Close to NN155A; at the apex and central vein, close to 146C; color does not change with subsequent development. Outer perianth, lateral segments: Length: About 5.8 cm to 6 cm. Width: About 4.3 cm to 4.6 cm. Shape: Obovate. Apex: Cuspidate. Base: Cuneate. Margin: Shallowly serrate; slightly undulate. Texture and luster, upper and lower surfaces: Smooth, glabrous; matte. Color, when opening, upper and lower surfaces: Close to 155A. Color, fully opened, upper surface: Close to 155C; at the apex, close to 137B; venation, close to 189B. Color, fully opened, lower surface: Close to 155A. Outer perianth, median segment: Length: About 5.5 cm to 5.8 cm. Width: About 4.3 cm to 4.5 cm. Shape: Obovate. Apex: Cuspidate. Base: Cuneate. Margin: Shallowly serrate; slightly undulate. Texture and luster, upper and lower surfaces: Smooth, glabrous; matte. Color, when opening, upper and lower surfaces: Close to 155A. Color, fully opened, upper surface: Close to 155C; at the apex, close to 137B; venation, close to 189B. Color, fully opened, lower surface: Close to 155C.

*Pedicels*.—Length: About 5 mm to 10 mm. Diameter: About 1.5 mm to 2 mm. Strength: Strong. Angle: About 30° from vertical. Texture and luster: Smooth, glabrous; matte. Color: Close to 137D.

*Reproductive organs*.—Stamens: Quantity per flower: Typically six. Filament length: About 3.5 cm. Filament color: Close to 69A. Anther shape: Elliptical. Anther size: About 2 mm by 1 mm. Anther color: Close to 160B. Pollen amount: Moderate. Pollen color: Close to 13A. Pistils: Quantity per flower: One. Pistil length: About 4.3 cm. Style length: About 4.1 cm. Style color: Close to 69A. Stigma diameter: About 1 cm. Stigma shape: Three-parted. Stigma color: Close to 69D. Ovary color: Close to 145A.

*Fruits and seeds*.—To date, fruit and seed development have not been observed on plants of the new *Alstroemeria*.

Pathogen & pest resistance: To date, plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain, temperatures from about −5° C. to about 40° C. and to be suitable for USDA Hardiness Zone 9.

It is claimed:

1. A new and distinct *Alstroemeria* plant named 'Zapriclare' as illustrated and described.

* * * * *